United States Patent [19]

Dang et al.

[11] Patent Number: 5,136,082
[45] Date of Patent: Aug. 4, 1992

[54] PROCESS FOR PREPARING ORGANIC ESTERS AND AMIDES AND CATALYST SYSTEM THEREFOR

[75] Inventors: Vu A. Dang, Wilmington, Del.; Gleason O. Cookson, Taunton, Mass.; Krishna Raman, Wilmington, Del.

[73] Assignee: Himont Incorporated, Wilmington, Del.

[21] Appl. No.: 562,515

[22] Filed: Aug. 3, 1990

[51] Int. Cl.⁵ .................................. C07C 69/76
[52] U.S. Cl. ........................ 560/75; 564/167
[58] Field of Search ..................... 560/75; 564/167

[56] References Cited

U.S. PATENT DOCUMENTS

| | | | |
|---|---|---|---|
| 3,920,729 | 11/1975 | Sugawa et al. | 560/75 |
| 3,984,460 | 10/1976 | Spivack et al. | 560/75 |
| 3,988,363 | 10/1976 | Spivack et al. | 560/75 |
| 4,228,297 | 10/1980 | Haeberii et al. | 560/75 |
| 4,536,593 | 8/1985 | Orban et al. | 560/75 |
| 4,547,585 | 10/1985 | Yamanaka et al. | 560/75 |
| 4,618,700 | 10/1986 | Gubler et al. | 560/75 |

*Primary Examiner*—Paul J. Killos

[57] ABSTRACT

Disclosed is a process for the preparation of organic esters and amides by reacting (a) a 5 to 60 mole % excess of an ester of (substituted-4-hydroxyphenyl) alkanoic acid with (b) (i) a $C_4$–$C_{20}$ aliphatic alcohol or thioether alcohol having one or more hydroxyl groups or (ii) an amine of the formula, $(R''')_2N(CH_2)_nR''''$ wherein $R'''$ is hydrogen, $C_{1-7}$ alkyl, $C_{5-12}$ cycloalkyl, or $C_{6-12}$ aryl, provided that one $R'''$ is hydrogen, and $R''''$ is hydrogen or $N(R''')_2$ wherein $R'''$ is a defined above, in the presence of a catalyst system comprising a basic inorganic compound and a polar aprotic organic compound. The process provides higher yields of the desired product, shorter reaction times, and reduces the production of undesirable side-products.

18 Claims, No Drawings

PROCESS FOR PREPARING ORGANIC ESTERS AND AMIDES AND CATALYST SYSTEM THEREFOR

FIELD OF THE INVENTION

This invention relates to a process for the preparation of organic esters and amides from certain organic esters. More particularly this invention relates to a process for the preparing organic esters and amides from esters of (substituted-4-hydroxyphenyl)alkanoic acid using a catalyst system comprising a basic inorganic compound and a polar aprotic organic compound.

BACKGROUND OF THE INVENTION

It is known to transesterify and amidify esters, for example methyl 3-(3,5,di-t-butyl-4-hydroxyphenyl) propionate, with alcohols, such as pentaerythritol, dipentaerythritol, stearyl alcohol, 1,6-hexanediol, 2,2'-thiodiglycol and neopentylglycol, or with amines, such as N-methylamine, N-cyclopropylamine, ethylenediamine and tetramethylenediamine, in the presence of a basic catalyst, such as lithium amide, sodium t-butoxide, potassium hydroxide, and sodium N-methyl-N-phenylamide, in the presence of solvent, such as tetralin or toluene, to form the ester or amide of the alcohol or amine, respectively, employed and methanol as the by-product.

For example, U.S. Pat. No. 4,288,297 describes the transesterification of the above propionate in an inert solvent, such as tetralin, which is used to assist in the removal of the methanol by-product of the reaction. However, the yield from this process is low, and it can lead to peroxide formation, and, in some cases, to undissolved alcohol or amine. U.S. Pat. No. 4,547,858 discloses a process of reacting the above propionate with pentaery-thritol in the presence of a solvent and water, whereby the solvent is distilled off prior to the neutralization of the reaction mixture.

In another process disclosed in U.S. Pat. No. 4,618,700, a 15-50 mol % excess of the propionate is used in place of the inert solvent to assist in the removal of the methanol. While the yield with this process is good, the reaction temperature and pressure are quite severe, e.g. 200° C. at 7 mbar.

To obtain high conversion yield, it is necessary to run such reactions at higher temperatures, i.e. about 180° C. or more, which results in a product having significant discoloration, or to run such reactions for long reaction times, or both. When lower temperatures and times are used, the conversion is reduced.

SUMMARY OF THE INVENTION

The present invention provides a process for preparing organic esters and amines by reacting (a) a 5 to 60 mole % excess of an organic ester having the following general formula:

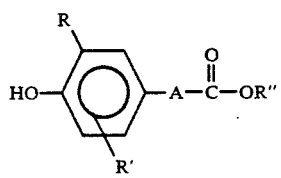

where R and R' are a $C_1$-$C_{12}$ linear or branched alkyl, a $C_5$-$C_{12}$, cycloalkyl, a $C_6$-$C_{12}$ aryl, or a $C_7$-$C_{12}$ alkaryl or aralkyl and may be the same or different, A is a $C_{1-6}$ linear or branched alkylene or a single direct bond and R" is methyl or ethyl, with (b) (i) a $C_4$-$C_{20}$ linear and branched aliphatic alcohol or thioether alcohol having one or more hydroxyl groups or (ii) an amine of the formula, $(R''')_2N(CH_2)_nR''''$ wherein R''' is hydrogen, $C_{1-7}$ alkyl, $C_{5-12}$ cycloalkyl, or $C_{6-12}$, provided that one R''' is hydrogen, and R'''' is hydrogen or $N(R''')_2$ wherein R''' is as defined above, and n is a number from 0-8, in the presence of a basic inorganic compound/polar aprotic organic compound catalyst system, at a temperature from 60° to 185° C. and under vacuum or under a flow of an inert gas at atmospheric pressure. When R''' is other than hydrogen, it is preferably methyl or ethyl.

DETAILED DESCRIPTION OF THE INVENTION

While as little as 5 mole % excess or as much as 60 mole % excess of the organic ester can be used in the practice of this invention, it is preferred to use from 15 to 30 mole % excess, most preferably from 20 to 30 mole % excess based on the total number of hydroxyl groups on the alcohol or, where an amine is used, the total number of amino groups on the amine.

Suitable alcohols include n-hexyl alcohol, n-octyl alcohol, stearyl alcohol, 1,6-hexanediol, 2,2'-thioglycol, neopentylglycol, pentaerythritol, and dipentaerythritol. Preferred is pentaerythritol.

Useful amines include aliphatic monoamines, such as N-methylamine, N,N-diethylamine and N-cyclohexylamine; diamines, such as ethylene diamine, 1,3-diaminopropane tetramethylenediamine and hexamethylenediamine. Hexamethylenediamine is preferred.

The basic inorganic compounds useful in the practice of this invention are alkali metal compounds, such as alkali metal hydride, alkali metal hydroxides, alkali metal alkoxides, alkali metal amides and alkali metal alkyl amides. Alkali metals for the basic compounds include lithium, sodium and potassium. Examples of the basic inorganic compounds useful in the present invention are lithium hydride, sodium hydride, lithium hydroxide, sodium hydroxide, potassium hydroxide, potassium methoxide, sodium methoxide, lithium methoxide, potassium ethoxide, sodium ethoxide, lithium ethoxide, potassium tert-butoxide, sodium tert-butoxide, n-butyllithium, phenyl potassium, phenyl sodium, lithium amide, potassium amide and lithium diisopropyl amide. Preferred is lithium amide. The basic inorganic compound is typically present in an amount from about 1 to 30 mole % per mole of alcohol or amine used. Preferably, the base inorganic compound is present in an amount of from about 2 to 15 mole %, and most preferably, from 5 to 7 mole % per mole of alcohol or amine.

In order for a polar aprotic organic compound to be useful as a co-catalyst in the practice of this invention, it must have sufficient polarity to dissolve the particular ingredients employed at the reaction temperature used and it must be capable of complexation with the metal ion of the basic inorganic compound used. Such polar aprotic organic compounds include N-methylpyrrolidinone (NMP), 1,2-dimethoxybenzene (DMB), N,N-dimethylacetamide (DMAC), hexamethyltriphosphoramide, tetramethylenesulfone, tetraethylene glycol dimethyl ether, ethylene glycol dimethylether, dimethylformamide (DMF), dimethylaminopyridine (DMAP), N,N,N',N'-tetramethylethylenediamine (TMEDA) and 1,3-dimethyl-2-imidazolidinone (DMI). Dimethylsulfoxide (DMSO), tetrahydrofuran (THF) and crown ethers, such as 12-crown-4, can also be used as the solvent and co-catalyst and are within the broadest aspects of the invention. However, THF is toxic and may leave impurities in the final products making them unacceptable for use in the manufacture of plastic articles to be used in contact with food, medicines, pharmaceuticals and other materials which are eaten, taken orally or intravenously or topically applied. The crown ethers are highly toxic and, thus, would have the same limitations as the THF compound. NMP, DMI, DMB and DMAC are preferred, with NMP being the most preferred.

Organic esters and amides obtained from the process of this invention include n-octyl-$\beta$-(3,5-di-t-butyl-4-hydroxyphenyl)propionate, n-octadecyl-$\beta$-(3,5-di-t-butyl-4-hydroxyphenyl)propionate, N-cyclohexyl-$\beta$-(3,5-di-t-butyl-4-hydroxyphenyl)propionamide, ethylene-bis-$\beta$-(3,5-di-t-butyl-4-hydroxyphenyl)propionate, 1,2-bis-(3-(3-methyl-5-isopropyl-4-hydroxyphenyl)propionamido)ethane, pentaerythritol tetrakis-[3-(3'-methyl-5'-t-butyl-4'-hydroxyphenyl)propionate], N,N'-hexamethylene bis(3,5-di-tert-butyl-4-hydroxy)hydrocinnamamide and pentaerythritol tetrakis-(3,5-di-t-butyl-4-hydroxyphenyl)propionate.

According to the process of this invention, an excess of the organic ester of the formula described above is reacted with (i) an alcohol or thioether alcohol or (ii) an amine in the presence of a polar aprotic organic compound at a temperature of from 60°-130° C. The basic inorganic compound is added and the reaction mixture is heated to a temperature of from 100°-185° C. while continuously sparging with an inert gas, such as nitrogen gas, at atmospheric pressure or under vacuum. The inert gas or vacuum facilitates the removal of the by-product. Preferably the process is carried out under a flow of inert gas at atmospheric pressure.

As used in the present invention, the term "by-product" refers to the alkanol formed during the transesterification or amide synthesis, and "side-product" refers to any product other than the desired product which may be formed during the transesterification or amide synthesis.

The order of addition of the polar aprotic organic compound and the basic inorganic compound to the reaction medium containing the ester and alcohol or amine is not critical, since the reaction between reactants does not start until all of the reactants are present. The basic inorganic compound can be introduced into the reaction medium before the polar aprotic organic compound. Preferably, the polar aprotic organic compound is added to the reaction mixture first, in order to decrease the viscosity of the reaction mixture.

When sparging with an inert gas, such as nitrogen, in the practice of this invention, the sparging is done at a flow rate of from 0.2 L/min. to 1 L/min., preferably from 0.5 to 1 L/min., most preferably at a low rate of about 0.2 L/min., at ambient pressure, until the reaction is about 50 to 70% complete and then at a higher rate of from 0.5 to 1 L/min. for the remainder of the reaction time.

When the removal of the by-product is carried out under a vacuum, the pressure must be low enough to effectively remove the by-product. The pressure can be from 1 mmHg to 200 mmHg, preferably from 5 to 150 mmHg, and most preferably from 10 to 30 mmHg. Also, solvent refluxation plays an important role when the vacuum process is used, in that it aids in the removal of the by-product and accelerates the transesterification reaction.

Most preferably, the reaction mixture is rapidly agitated during the removal of the by-product to form homogeneous mixture thereby preventing the trapping of the by-product within the reaction medium which is somewhat viscous. The reaction is typically agitated from about 450 rpm to about 2000 rpm in a lab scale reaction. In a commercial scale process, typical commercial turbine mixers would be used to provide sufficiently rapid mixing.

Once the by-product has been removed, the reaction medium is then neutralized with an acid, such as glacial acetic acid, at a temperature of from 100°-110° C. After about 5-25 minutes, the reaction mass is crystallized from methanol and water to yield the final product.

The temperature range for carrying out the reaction of the present invention is from 60°-185° C., preferably from 100°-155° C.

The present invention is illustrated in greater detail by the examples of the invention set forth below.

All parts and percentages are by weight unless otherwise indicated.

EXAMPLE 1

To a reaction vessel equipped with a mechanical stirrer, thermometer, condenser, a trap and nitrogen sparge tube are added 94.5 g (60 mole % excess) methyl 3-(3,5-di-t-butyl-4-hydroxyphenyl)propionate, 6.8 g pentaerythritol and 13 ml N-methylpyrrolidone (NMP) and heated to 120° C. Then 0.083 g lithium amide is added with agitation and the reaction mixture is heated to 140° C. at atmospherhic pressure while continuously sparging with nitrogen gas at a rate of 1 L/min. for 1.5 hours. Analysis by high pressure liquid chromatography indicated that 99% of tetrakis [3-(3,5-di-t-butyl-4-hydroxyphenyl)propionyloxymethyl]methane is obtained, based on the pentaerythritol.

CONTROL EXAMPLE 1

The procedure and ingredients of Example 1 are used except that tetralin is used instead of NMP. After 3.5 hours, 96% of tetrakis [3-(3,5-di-t-butyl-4-hydroxyphenyl) propionyloxymethyl]methane is obtained, based on the pentaerythritol.

CONTROL EXAMPLE 1A

The procedure and ingredients of Example 1 are used except for NMP, in other words, the reaction is neat. After 2.5 hours, 98% of tetrakis [3-(3,5-di-t-butyl-4-hydroxyphenyl)propionyloxymethyl]methane is obtained, based on the pentaerythritol.

EXAMPLE 2

The procedure and ingredients of Example 1 are used except that 64.5 g (10 mole % excess) of the propionate and 9 ml of NMP are used. After 3.0 hours, 99% of tetrakis [3-(3,5-di-t-butyl-4-hydroxyphenyl)propionyloxymethyl]methane is obtained, based on the pentaerythritol.

CONTROL EXAMPLE 2

The procedure and ingredients of Example 2 are used except that tetralin is used instead of NMP. After 6.5 hours, 90% of tetrakis [3-(3,5-di-t-butyl-4-hydroxyphenyl) propionyloxymethyl]methane is obtained, based on the pentaerythritol.

CONTROL EXAMPLE 2A

The procedure and ingredients of Example 2 are used except for NMP, in other words, the reaction is neat. After 2.5 hours, 92% of tetrakis [3-(3,5-di-t-butyl-4-hydroxyphenyl)propionyloxymethyl]methane is obtained, based on the pentaerythritol.

EXAMPLE 3

The procedure and ingredients of Example 1 are used except that 0.15 g of 12-crown-4 ether are used instead of NMP. After 2.0 hours, 93% of tetrakis [3-(3,5-di-t-butyl-4-hydroxyphenyl)propionyloxymethyl]methane is obtained, based on the pentaerythritol.

As demonstrated by examples 1 and 2 of the present invention, good yields of the product are obtained in a reduced amount of time as compared to control examples 1, 1A, 2 and 2A where a conventional solvent or no solvent at all is used.

EXAMPLE 4

To a reaction vessel equipped with a condenser, a thermometer, a trap and a mechanical stirrer are added 76 g (30 mole % excess) of methyl 3-(3,5-di-t-butyl-4-hydroxyphenyl) propionate, 6.8 g of pentaerythritol and 8 ml of N,N-dimethylacetamide (DMAC) and heated to 120° C. Then 0.85 g of lithium amide is added to the reaction mixture. With agitation and under a vacuum of 90 mmHg, the reaction mixture is heated to 140° C. and the DMAC is refluxed. After 2.5 hours, analysis by high pressure liquid chromatography indicated that 96% of tetrakis [3-(3,5-di-t-butyl-4hydroxyphenyl)propionyloxymethyl]methane is obtained, based on the pentaerythritol.

EXAMPLE 5

To a reaction vessel equipped with a condenser, a thermometer, a trap, a nitrogen sparge tube and a mechanical stirrer are added 43 g (10 mole % excess) methyl 3-(3,5-di-t-butyl-4-hydroxyphenyl)propionate, 5 g 1,3-diaminopropane and 5 ml of N-methylpyrrolidone (NMP). Then 0.1 g of lithium amide is added with agitation and the reaction mixture is heated to 100° C. at atmospheric pressure while continuously sparging with nitrogen gas at a rate of 0.3 L/min. for 2.5 hours. Analysis by high pressure liquid chromatography indicated that 90% of 1,3-bis-[3-(3,5-di-t-butyl-4-hydroxyphenyl)-propionamido] propane is obtained.

EXAMPLE 6

To a reaction vessel equipped with a condenser, a thermometer, a trap, a nitrogen sparge tube and a mechanical stirrer are added 307 g (5 mole % excess) methyl 3-(3,5-di-t-butyl-4-hydroxyphenyl) propionate, 270.5 g commercial stearyl alcohol and 10 wt % of N-methylpyrrolidinone (NMP). Then 2 mole % of lithium amide is added with agitation and the reaction mixture is heated to 115°-155° C. at atmospheric pressure while continuously sparging with nitrogen gas at a rate of 0.5 L/min. for 1.5 hours. Analysis by gas chromatography indicated that 99.9% of octadecyl 3-(3,5-di-t-butyl-4-hydroxyphenyl) propionate is obtained.

EXAMPLE 7

To a reaction vessel equipped with a mechanical stirrer, thermometer, condenser, a trap and nitrogen sparge tube are added 94.5 g (60 mole % excess), methyl 3-(3-5-di-butyl-4-hydroxyphenyl)propionate, 6.8 g pentaerythritol and 13 mL dimethoxybenzene (DMB) and heated to 100° C. Then 7 mole % lithium amide is added with agitation and the reaction mixture is heated to 150° C. at atmospheric pressure while continuously sparging with nitrogen gas at a rate of 0.5 L/min. for 2 hours. Analysis by high pressure liquid chromatography indicated that 98.5% of tetrakis [3-(3,5-di-t-butyl-4-hydroxyphenyl)propionize methyl]methane is obtained, based on the pentaerythritol.

Thus the process of the present invention provides a reduction in reaction time and reduces the formation of undesirable side-products, such as the tris product when pentaerythritol is used.

The products produced by the process of the present invention are known and can be used as antioxidants in materials which are subject to degradation, such as plastics, rubbers and other polymers.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

We claim:

1. A process for preparing organic esters and amides by reacting (a) 5 to 60 mole % excess of an organic ester of the formula:

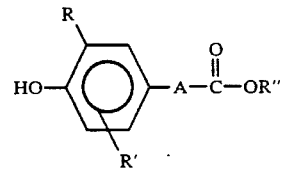

where R and $R^1$ are a $C_1$-$C_{12}$ linear or branched alkyl, a $C_5$-$C_{12}$ cycloalkyl, a $C_6$-$C_{12}$ or a $C_7$-$C_{12}$ alkaryl or aralkyl and may be the same or different, A is a $C_1$-$C_6$ linear or branched alkylene or a single direct bond and R" is methyl or ethyl, with (b) (i) a $C_4$-$C_{20}$ linear or branched aliphatic alcohol or thioether alcohol having one or more hydroxyl groups or (ii), an amine of the formula, $(R''')_2N(CH_2)_nR''''$ wherein R''' is hydrogen, $C_{1-7}$ alkyl, $C_{5-12}$ cycloalkyl, or $C_{6-12}$ aryl, provided that one R''' is hydrogen, and R'''' is hydrogen or $N(R''')_2$ wherein R''' is a defined above, and n is a number from 0-8, in the presence of a polar aprotic organic compound and basic inorganic compound catalyst system under vacuum or under a flow of inert gas to remove the by-product.

2. A process according to claim 1, wherein (b) is (i) an alcohol.

3. A process according to claim 2, wherein said aliphatic alcohol is selected from the group consisting of n-hexyl alcohol, n-octyl alcohol, stearyl alcohol, 1,6-hexanediol, neopentylglycol, pentaerythritol and dipentaerythritol.

4. A process according to claim 3, wherein said is pentaerythritol.

5. A process according to claim 1, wherein (b) is (ii) an amine of the formula, $(R''')_2N(CH_2)_nR''''$ wherein R''' is hydrogen, $C_{1-7}$ alkyl, $C_{5-12}$ cycloalkyl, or $C_{6-12}$ aryl, provided that one R''' is hydrogen, and R'''' is hydrogen or N(R''')₂ wherein R''' is a defined above, and n is a number from 0-8.

6. A process according to claim 5, wherein said amine is selected from the group consisting of N-methyl amine, N,N-diethylamine, N-cyclohexylamine, ethylene diamine, 1,3-diaminopropane, tetramethylenediamine and hexamethylenediamine.

7. A process according to claim 6, wherein said amine is hexamethylenediamine.

8. A process according to claim 1, wherein said polar aprotic organic compound is selected from the group consisting of N-methylpyrrolidinone, 1,2-dimethoxybenzene, N,N-dimethylacetamide, hexamethyltriphosphoramide, dimethylformamide, dimethylaminopyridine, tetramethylenesulfone, tetramethyl glycol dimethylether, ethylene glycol dimethylether, N,N,N',N'-tetramethylethylenediamine, 1,3-dimethyl-2-imidazolidinone, dimethylsulfoxide, tetrahydrofuran and 12-crown-4.

9. A process according to claim 8, wherein said polar aprotic organic compound is N-methylpyrrolidone.

10. A process according to claim 1, wherein said basic inorganic compound is selected from the group consisting of alkali metal hydroxides, alkali metal alkoxides, alkali metal amides, alkali metal alkyl amides and alkali metal hydrides.

11. A process according to claim 10, wherein said basic inorganic compound is selected from the group consisting of potassium methoxide, sodium methoxide, lithium methoxide, potassium ethoxide, sodium ethoxide, lithium ethoxide, potassium-t-butoxide, sodium-t-butoxide, lithium amide, n-butyllithium amide, lithium diisopropyl amide, potassium amide, lithium hydride and sodium hydride.

12. A process according to claim 11, wherein said basic inorganic compound is lithium amide.

13. A process according to claim 1, wherein the reaction temperature is from 60°-185° C.

14. A process according to claim 1 which is conducted under vacuum.

15. A process according to claim 1 which is conducted under a flow of an inert gas.

16. A process according to claim, 1 wherein said basic inorganic compound is present in the amount of from 1 to 30 mole % per mole of alcohol or amine.

17. A process according to claim 12, wherein said basic inorganic compound is present in the amount of 5 to 7 mole % per mole of alcohol or amine.

18. A process according to claim 8, wherein said polar aprotic organic compound is 1,2-dimethoxybenzene.

* * * * *